United States Patent
Zhou et al.

(10) Patent No.: US 6,265,451 B1
(45) Date of Patent: *Jul. 24, 2001

(54) SKELETAL IRON CATALYST AND ITS PREPARATION FOR FISCHER-TROPSCH SYNTHESIS PROCESSES

(75) Inventors: Jinglai Zhou; Yijun Lu; Zhixin Zhang; Guohui Li; Linyao Dong; Hairong Wang, all of Shanxi (CN); Peizheng Zhou, Lawrenceville; Lap-Keung Lee, West Windsor, both of NJ (US)

(73) Assignee: Hydrocarbon Technologies, Inc., Lawrenceville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/399,853

(22) Filed: Sep. 21, 1999

(51) Int. Cl.$^7$ .............................. C07G 27/00; B01J 23/00; B01J 5/00; B01J 23/40; C22C 38/06
(52) U.S. Cl. ..................... 518/700; 502/314; 502/327; 502/301; 502/331; 502/332; 502/336; 502/338; 420/77; 420/590; 420/89; 420/90; 420/91
(58) Field of Search ..................... 502/301, 314, 502/327, 331, 336, 338, 332; 420/77, 590, 89, 90; 518/700; 421/91

(56) References Cited

U.S. PATENT DOCUMENTS 3,862,911 * 1/1975 Chabert .................. 252/470

OTHER PUBLICATIONS

Lupei et al, catalytic activity of skeletal iron catalyst, Tekhnot Inst., Voronezh, USSR, Gos. Univ. (1966) No. 4 108–110, 1966.*

* cited by examiner

*Primary Examiner*—Johann Richter
*Assistant Examiner*—J. Parsa
(74) *Attorney, Agent, or Firm*—Fred A. Wilson

(57) ABSTRACT

Skeletal iron catalysts are prepared and utilized for producing hydrocarbon products from CO and $H_2$ feeds by Fischer-Tropsch synthesis process. Iron powder is mixed with aluminum, antimony, silicon, tin or zinc powder and 0.01–5 wt % metal promotor powder to provide 20–80 wt % iron content, then melted together, cooled to room temperature and pulverized to provide 0.1–10 mm iron alloy catalyst precursor particles. The iron alloy precursor particles are treated with NaOH or KOH caustic solution at 30–95° C. to extract or leach out a major portion of the non-ferrous metal portion from the iron, and then dried and reduced under hydrogen atmosphere to provide the skeletal iron catalyst material. Such skeletal iron catalyst is utilized with $CO+H_2$ feedstream in either fixed bed or slurry bed type reactor at 200–350° C. temperature, 1.0–3.0 mPa pressure and gas hourly space velocity of 0.5–3.0 L/g Fe/h to produce desired hydrocarbon products.

17 Claims, No Drawings

SKELETAL IRON CATALYST AND ITS PREPARATION FOR FISCHER-TROPSCH SYNTHESIS PROCESSES

BACKGROUND OF THE INVENTION

This invention pertains to skeletal iron catalysts, and particularly pertains to catalyst composition and preparation methods and processes for use of such skeletal iron catalysts in Fischer-Tropsch synthesis processes for CO and $H_2$ feeds to produce hydrocarbon products.

As a basic technology for producing synthetic liquid fuels from $CO+H_2$ feedstreams, the Fischer-Tropsch (F-T) catalytic synthesis process has undergone worldwide development and use since the 1920s. Iron-based catalysts have been widely investigated and used, and precipitated iron catalyst and fused iron catalyst have been the commonly used catalysts in such F-T synthesis processes. However, the preparation procedure for the precipitated iron catalyst is undesirably complicated and includes several steps of precipitation, washing, filtration, drying, formation, calcination, pulverization, and reduction. Also, the precipitated iron catalyst is significantly influenced by various parameters, including precipitating agent, solution concentration, precipitation temperature, solution pH value, pretreatment temperature, and atmosphere, and such catalyst is undesirably expensive. Furthermore, the fused iron catalyst has undesirably low active surface area (~10 $m^2/g$) that is difficult to increase, and it also has low catalytic activity and minimal economic advantage. Both of these two known iron catalysts provide only conventional hydrocarbon product selectivity. On the other hand, since development of the known skeletal nickel catalyst systems, such skeletal type catalysts have been used in organic reactions, particularly in liquid phase hydrogenation systems. Some previous development work has been focused on skeletal nickel catalyst and worked only on some simple hydrogenation reaction systems. Because of the desirability for improving the activity and selectivity of iron catalyst for Fischer-Tropsch synthesis processes, development of an improved skeletal iron catalyst was initiated.

SUMMARY OF THE INVENTION

The present invention provides a skeletal iron catalyst which is uniquely suitable for Fischer-Tropsch synthesis of CO and $H_2$ feedstreams for producing desired hydrocarbon products. This unique skeletal iron catalyst material contains 40–90 wt % iron with the remainder being smaller percentage of non-ferrous metals selected from aluminum, antimony, silicon, tin, or zinc together with less than 5 wt % of promotor metal selected from calcium, copper, chromium, magnesium or potassium, and has surface area of 25–65 $m^2$/gm. This skeletal iron catalyst is made using a preparation method including providing an iron powder mixed with a suitable non-ferrous metal powder selected from aluminum, antimony, silicon, tin, or zinc sufficient to provide 20–80 wt. % iron together with 0.01–5 wt. %, of a non-ferrous promotor metal powder including calcium, copper, chromium, magnesium, or potassium. The mixed metal powders are heated and melted together so as to form an iron alloy precursor material, followed by pulverizing the iron alloy to 0.1–10 mm particle size, and then extracting and/or leaching a major portion of the non-ferrous metal portion from the iron alloy using a suitable caustic solution such as NaOH or KOH and after drying and reducing with hydrogen leaving the iron particles as a skeletal iron alloy catalyst material. The catalyst final particle size can be within a 20–10,000 micron range, with the larger size particles within this range being intended for F-T fixed bed reactor usage and the smaller size particles up to about 2000 micron within this range intended for slurry phase bed reactor usage.

The resulting skeletal iron catalyst which contains 50–90 wt % iron has high activity and provides good selectivity towards the formation of desirable low-molecular-weight hydrocarbon products from the CO and $H_2$ feedstreams. This skeletal iron catalyst has catalytic activity equivalent to that of precipitated iron catalyst, and product selectivity exceeding that of either precipitated or fused iron catalysts, and can be utilized in either fixed bed or slurry bed type reactors for Fischer-Tropsch synthesis reaction processes for producing the desired hydrocarbon products.

The skeletal iron catalyst of this invention has various advantages compared with the conventional precipitated iron or fused iron catalysts for Fischer-Tropsch synthesis processes; which advantages include:

(a) The preparation method and pretreatment procedures for skeletal iron catalyst are relatively simple and inexpensive.

(b) Specific surface area of skeletal iron catalyst (25–65 $m^2$/g) can approach that of precipitated iron catalyst and exceeds that of fused iron catalyst.

(c) Synthesis feed gas conversion using skeletal iron catalyst (CO conversion>90%) is equivalent to that achieved by precipitated iron catalyst and exceeds that achieved by fused iron catalyst for equivalent space velocities.

(d) For slurry-phase Fischer-Tropsch synthesis processes, the skeletal iron catalyst has stable activity and significant selectivity for low molecular weight hydrocarbon products ($C_4$ selectivity>10%).

DESCRIPTION OF INVENTION

The skeletal iron catalyst of this invention is prepared by using a preparation method which includes the following three basic steps:

1. Preparation of Catalyst Precursor Particles

Provide and mix together iron powder and a non-ferrous metal powder selected from aluminum, antimony, silicon, tin, or zinc in weight proportion having iron content of 20–80 wt. %, and 0.01–5.0 wt. % of a promotor metal powder selected from calcium, copper, chromium, potassium or magnesium, and place the mixed metals powders into a suitable furnace such as an electric arc induction furnace. Then ignite an electric arc with suitable high current and low voltage under an inert gas protection of argon or nitrogen, and stir the metal powders uniformly under a magnetic field to heat and melt the powders. Then cool the molten iron alloy material to room temperature and mechanically pulverize the resulting metal alloy to provide iron alloy precursor particles having 0.1–10 mm particle size.

2. Preparation of Skeletal Iron Catalyst

The skeletal iron catalyst is prepared from the iron alloy precursor particles under hydrogen atmosphere protection, using either one of the following three procedures:

(a) Add a sufficient volume of NaOH or KOH caustic solution (10–50% concentration) into a stirred container, heat the solution to a temperature of 30°–95° C., add the iron alloy precursor particles (0.1–10 mm size) into the caustic solution, and maintain the reaction condition for 2–150 minutes after the metal alloy particle addition to extract and/or leach out a major portion of the non-ferrous metal portion from the treated iron alloy particles which now contain 40–90 wt. % iron. Then wash the treated iron particles with deionized water to pH=7, replace water with water-free ethanol, and temporarily store the resulting skeletal iron catalyst particles in ethanol.

(b) Mechanically mix uniformly the iron alloy precursor catalyst particles and solid sodium hydroxide powder at weight ratio to the iron alloy powder of 5–10:1, add deionized water drop-wise to wet the mixture into a paste form but not in a fluid state, while stirring to allow the reaction to proceed in a desired moisture content. After the reaction has proceeded for 5–30 minutes and gas release has gradually decreased, add fresh NaOH or KOH solution (10–50% concentration), maintain for 2–60 minutes at 50–95° C., to extract and remove a major portion of the non-ferrous metal portion from the iron alloy particles. Then wash the resulting skeletal iron particles with deionized water to pH=7, displace water with water-free ethanol, and store the resulting skeletal iron catalyst particles in ethanol.

(c) Place iron alloy precursor particles in a well-stirred container, spray (preferably in the mist form) high-concentration (40–60%) NaOH or KOH solution onto the particles while stirring, maintain reaction in a wet state but not fluid state for 5–30 minutes, then add additional NaOH or KOH solution of 10–50% concentration, and maintain for a period of 2–60 minutes at 50–95° C. to extract and remove a major portion of the non-ferrous metal portion from the iron alloy particles. Then wash the resulting iron skeletal iron alloy particles with deionized water to pH=7, displace water with water-free ethanol, and store the resulting skeletal iron catalyst particles in ethanol.

3. Pretreatment of Skeletal Iron Catalyst

Before reaction evaluation of the skeletal iron catalyst particles prepared in Step 2(a), 2(b) or 2(c), the catalyst stored in water-free ethanol is screened to remove undesired sized particles before the pretreatment step. This pretreatment can be done via either of two routes. The first route is to place the catalyst in a porcelain boat inside a tubular reactor and dry and reduce the catalyst with high space velocity hydrogen at 2001–500° C. for 2–12 hours, then screen, weigh, and transfer the pretreated skeletal iron catalyst under high-purity nitrogen into water-free ethanol for evaluation or use in either a fixed-bed F-X reactor, or into a liquid paraffin for evaluation or use in slurry-phase F-X reactor. The second pretreatment route is to screen the catalyst in water-free ethanol, then dry and reduce the catalyst in a curved quartz-tube under hydrogen atmosphere at 100–200° C., then transfer the pretreated skeletal iron catalyst into either water-free ethanol or liquid paraffin for evaluation or use as before.

Process Utilizing Skeletal Iron Catalyst

The skeletal iron catalyst of this invention is uniquely useful in catalytic processes for Fischer-Tropsch synthesis of CO and $H_2$ feedstreams to produce desired hydrocarbon products. Useful reaction conditions for slurry bed reactor include 0.5–2.5:1 $H_2/CO$ molar ratio feedstreams and 4–20 wt. % catalyst loading relative to liquid paraffin as reaction medium, catalyst particle size of 0.02–2.00 mm, 200–350° C. temperature, 1.0–3.0 mPa pressure, and gas hourly space velocity of 0.5–3 L/g Fe/h.

The catalyst preparation method and use for this invention will be further disclosed by the following examples, which should not be construed as limiting in their scope.

EXAMPLE 1

1. Add metal iron and aluminum powders together with small amount of copper oxide promoter powder in respective weight ratio 49:50:1 into an electric-arc induction furnace, evacuate the air and fill the furnace with argon inert blanketing gas, then apply 450A, 25V electric current to induce an electric arc for heating and melting the metal powder materials uniformly during magnetic stirring. Then cool the iron-aluminum copper alloy material to room temperature and mechanically pulverize the alloy material to 0.1–10 mm particle size to produce iron alloy precursor material particles.

2. Under hydrogen atmosphere, add a volume of 25% concentration NaOH in a stirred container, heat to temperature of 85° C., then add the precursor iron alloy particles into the caustic solution at periodic time intervals, and maintain the reaction condition for 30 minutes to dissolve or extract a major portion of the aluminum from the iron alloy resulting iron particles. Then wash the particles with deionized water to pH=7, displace water with water-free ethanol and temporarily store the resulting skeletal iron catalyst in ethanol under refrigeration.

3. Before evaluating the stored skeletal iron catalyst in a F-T reaction system, dry and reduce the catalyst with ethanol in a porcelain boat inside a tubular reactor, at 300° C. for two hours with hydrogen at high space velocity, then screen and weigh in a container under high-purity nitrogen, and transfer the dried skeletal iron catalyst to slurry-phase reaction medium for evaluation.

4. Fischer-Tropsch synthesis conditions used for catalyst evaluation in a $CO/H_2$ feedstream within ranges of traditional research include catalyst loading of 6 wt. %, catalyst particle size of 0.062–0.075 mm, 2.0:1 $H_2/CO$ molar ratio, 270° C. temperature, 1.6 mPa pressure and reaction duration of 72 hours. Evaluation results are listed below in Table 1.

TABLE 1

Fischer-Tropsch Synthesis Results Using Skeletal Iron Catalyst and Traditional Iron Catalysts under Identical Reaction Conditions*

| | Skeletal Iron Catalyst | | | | | | Precipitated | Fused Iron |
|---|---|---|---|---|---|---|---|---|
| Example No. | 1 | 2 | 3 | 4 | 5 | 6 | Iron Catalyst | Catalyst |
| Catalyst Surface Area, M2/g | 25.0 | 37.8 | 42.5 | 45.6 | 58.6 | 64.5 | ~70 | 8.6 |
| CO Conversion, % | 94.25 | 94.53 | 95.78 | 94.36 | 89.59 | 91.22 | 92.59 | 83.77 |
| C4 Selectivity, %** | 9.2 | 17.5 | 15.5 | 20.2 | 19.7 | 16.4 | 6.5 | 11.4 |

*$H_2/CO$ = 2.0:1G HSV = 1.0h$^{-1}$, T = 270° C., P = 1.6 mPa
**C4/($C_1$–$C_6$) molar ratio

EXAMPLE 2

1. Add metal iron and aluminum power and a small amount of copper oxide at respective weight proportion or ratio of 25:74:1 into an electric-arc induction furnace, evacuate the air, and fill the furnace with argon gas for protection. Use 450A, 25V electric current to ignite electric arc for heating and melting the metal powders uniformly during magnetic stirring. Then cool the molten iron-aluminum copper alloy to room temperature, and mechanically pulverize the metal alloy material to 0.1–10 mm particle size to provide precursor iron alloy particles. Steps 2, 3 and 4 were the same as for Example 1. Evaluation results are provided in Table 1 above.

EXAMPLE 3

Add metal iron and aluminum powder and a small amount of copper oxide promoter at respective weight ratios of 33:66:1 in an electric-arc induction furnace, evacuate the air, and fill with argon gas for protection. Use 450A, 25V current to ignite electric arc to heat the metal powders and melt uniformly during magnetic stirring. Then cool metal alloy to room temperature, and mechanically pulverize to 0.1–10 mm precursor iron alloy particles. Steps 2, 3, and 4 were the same as for Example 1.

EXAMPLE 4

Provide iron-aluminum-copper alloy proportions the same as in Example 3, and provide the heating, melting, cooling and pulverizing Steps 1 and 2 the same as in Example 1. Before the catalyst stored in water-free ethanol is evaluated in a reaction system, screen the catalyst in water-free ethanol, dry and reduce the catalyst containing ethanol in a curved quartz tube at 200° C. under hydrogen flow, transfer catalyst into a slurry-phase reaction medium (liquid paraffin). Catalyst evaluation was the same as Step 4 in Example 1 and results are listed in Table 1.

EXAMPLE 5

Provide same iron-aluminum powder mixture proportions and heat, melt, cool and pulverize the metal alloy as in Example 1. Then mechanically mix uniformly the fine iron alloy catalyst precursor particles with solid sodium hydroxide (NaOH) powder, add deionized water drop-wise to wet the mixture into a paste but not in a fluid state, while stirring to allow reaction to proceed at desired moisture level. After gas released from reaction gradually decreases, transfer mixture into fresh 20% concentration NaOH solution, maintain for a time of 2–60 minutes at 55° C., then wash with deionized water to pH=7, displace water with water-free ethanol, and store catalyst in ethanol temporarily under refrigeration. Then pretreat the catalyst the same as in Example 4 and evaluate it the same as in Example 1.

EXAMPLE 6

Use an iron-aluminum-copper mixture as in Example 3. Place the pulverized fine size iron alloy precursor particles in a well-stirred container, spray (preferably in the mist form) 48% concentration NaOH or KOH solution onto the alloy particles while stirring, allow reaction to proceed in wet state but not fluid state for 20 minutes, then carefully add NaOH or KOH solution of 20% concentration and maintain for 30 minutes period of time at 55° C. Then wash with deionized water until pH value reaches 7, displace water with water-free ethanol, and store catalyst in ethanol. Pre-treat the catalyst the same as in Example 4, and evaluate it the same as in Example 1.

The six iron-aluminum copper alloy skeletal iron catalyst samples, which were prepared in Examples 1 through 6, were evaluated by F-T synthesis reaction using a CO and $H_2$ feedstream having $H_2$/CO molar ratio of 2.0:1 as for Example 1. Results of the catalyst evaluations are provided in Table 1 above.

From these results shown in Table 1 it is noted that surface areas for the skeletal iron catalyst examples approach that of the known precipitated iron catalyst and significantly exceed that of the fused iron catalyst. Also, CO conversion is generally equivalent to that for the precipitated iron catalyst and exceeds that for the fused iron catalyst Furthermore, the selectivity for $C_4$ product generally exceeds that for both the precipitated and fused iron catalysts.

We claim:

1. A method for preparing a skeletal iron catalyst useful for Fischer-Tropsch synthesis processes, comprising the steps of:

a) preparing a catalyst precursor metal alloy by providing iron powder together with non-ferrous metal powder selected from aluminum, antimony, silicon, tin or zinc sufficient to provide iron content of 20–80 wt. %, and adding 0.01–5.0 wt. % promotor metal powder selected from calcium, copper, chromium, magnesium, or potassium to provide a metal powder mixture; heating said metal powder mixture under inert gas protection while mixing said powders uniformly and melting the metal powders, then cooling the melted metal alloy to room temperature and pulverizing the resulting metal alloy to provide iron alloy precursor particles having 0.1–10 mm particle size;

b) treating said iron alloy precursor particles by contacting the particles with NaOH or KOH caustic solution under hydrogen atmosphere and heating the mixture to 30–95° C. temperature, while maintaining the treating conditions for 5–150 minutes and extracting and/or leaching out a major portion of the non-ferrous metal from the iron alloy particles which contain 40–90 wt. % iron, then washing the iron alloy particles with deionized water until pH=7, displacing the water with alcohol, and placing the resulting skeletal iron catalyst particles in ethanol; and c) pre-treating said skeletal iron catalyst particles by screening to provide 20–10,000 micron particle size and drying and reducing with hydrogen at high space velocity at 100–500° C. temperature for 2–12 hours, then transferring the dried skeletal iron catalyst into water-free ethanol or liquid paraffin for storage.

2. The skeletal iron catalyst preparation method of claim 1, wherein step (b) is treating said iron alloy precursor particles by adding sufficient NaOH or KOH caustic solution having 10–50% concentration into a stirred container under hydrogen atmosphere and heating the solution to 30–95° C. temperature, then adding the iron alloy precursor particles into the caustic solution at suitable time intervals, while maintaining the treating condition for 5–150 minutes after iron alloy particle addition for extracting and/or leaching out a major portion of the non-ferrous metal from the iron alloy particles, then washing the iron alloy particles with deionized water until pH=7, displacing the water with alcohol, and placing the resulting skeletal iron alloy catalyst particles in ethanol.

3. The skeletal iron catalyst preparation method of claim 1, wherein step (b) is mixing said iron alloy precursor particles with solid sodium hydroxide powder at weight ratio of sodium hydroxide to the iron alloy of 5–10:1, then adding deionized water drop-wise to wet the mixture to provide a paste but not a fluid state while stirring so that reaction proceeds under a wet state for 5–30 minutes while gas release gradually decreases, adding to said mixture fresh NaOH or KOH of 10–50% concentration solution and maintaining for 2–60 minutes at 50–95° C. temperature; then washing the iron alloy particles with deionized water to pH=7, displacing water with water-free alcohol and placing the resulting skeletal iron catalyst in ethanol.

4. The skeletal iron catalyst preparation method of claim 1, wherein step (b) includes placing the iron alloy precursor particles in a stirred container, spraying the particles with a 40–60% concentration NaOH or KOH solution, maintaining reaction in a wet but not fluid state for 5–30 minutes, adding NaOH or KOH solution of 10–50% concentration and maintaining for 2–60 minutes at 50–95° C. temperature, then washing the iron alloy particles with deionized water to pH=7, replacing the water with water-free alcohol and placing the resulting skeletal iron catalyst in ethanol.

5. The skeletal iron catalyst preparation method of claim 1, wherein said metal powder mixture includes iron, aluminum and copper having an initial respective weight ratio of 49:50:1.

6. The skeletal iron catalyst preparation method claim 1, wherein said metal powder mixture includes iron, aluminum and copper having an initial respective weight ratio of 25:74:1.

7. The skeletal iron catalyst preparation method claim 1, wherein said initial metal powder mixture includes iron, aluminum and copper having an initial respective weight ratio of 33:66:1.

8. A Fischer-Tropsch catalytic synthesis process for producing hydrocarbon products and utilizing skeletal iron catalyst in a reactor, the process comprising:

(a) feeding CO and $H_2$ gas having $H_2$/CO molar ratio of 0.5–2.5:1 into a reactor containing a skeletal iron catalyst prepared as defined by claim 1;

(b) maintaining said reactor at conditions of 200–350° C. temperature, 1.0–3.0 mPa pressure and gas hourly space velocity of 0.5–3.0 L/gFe/h; and (c) withdrawing from said reactor a hydrocarbon gas and hydrocarbon liquid product containing particles of said catalyst.

9. The catalytic synthesis process of claim 8, wherein the $H_2$/CO molar ratio is 2.0:1, reaction temperature is 270° C., pressure is 1.6 mPa and gas hourly space velocity is 1.0 L/gFe/h.

10. The catalytic synthesis process of claim 8, wherein the skeletal iron catalyst in ethanol having particle size of 0.1–10 mm (100–10,000 micron) is utilized in a fixed bed catalytic reactor.

11. The catalytic synthesis process of claim 8, wherein the skeletal iron catalyst having particle size of 0.02–0.2mm (20–200 micron) is utilized in a slurry phase catalytic reactor.

12. The skeletal iron catalyst preparation method of claim 1, wherein said non-ferrous metal is aluminum and said promotor metal is copper.

13. The skeletal iron catalyst preparation method of claim 1, wherein said metal powder mixture is heated and melted in an electric arc induction furnace during magnetic stirring.

14. The skeletal iron catalyst preparation method of claim 1, wherein the resulting skeletal iron catalyst particles contain 40–90 wt. % iron.

15. The skeletal iron catalyst preparation method of claim 1, wherein the catalyst final particle size is 0.1–10 mm intended for use in a fixed bed F-T catalytic reactor.

16. The skeletal iron catalyst preparation method of claim 1, wherein the catalyst final particle size is 20–2000 micron intended for use in a slurry bed catalytic F-T reactor.

17. A method for preparing a skeletal iron catalyst useful for Fischer-Tropsch synthesis processes, comprising the steps of:

a) preparing a catalyst precursor metal alloy by providing iron powder together with aluminum powder sufficient to provide iron content of 20–80 wt. %, and adding 0.01–5.0 wt. % copper promotor powder to provide a metal powder mixture; heating said metal powder mixture in an electric arc induction furnace under inert gas protection while mixing said powders uniformly by magnetic stirring and melting the metal powders, then cooling the melted precursor metal alloy to room temperature and pulverizing the metal alloy to provide iron alloy precursor particles having 0.1–10 mm particle size;

b) treating said iron alloy precursor particles by providing NaOH or KOH caustic solution having 10–50% concentration in a stirred container under hydrogen atmosphere and heating the solution to 30–95° C. temperature, then intermittently adding the iron alloy precursor particles into the caustic solution at suitable time intervals while maintaining the treating condition for 5–150 minutes after iron alloy particle addition and extracting and/or leaching out a major portion of the non-ferrous metals from the iron alloy particles which retain 40–90 wt. % iron, then washing the iron alloy particles with deionized water until pH=7, displacing the water with alcohol, and placing the resulting skeletal iron catalyst particles in ethanol; and c) pre-treating the skeletal iron catalyst particles by screening to provide 20–2000 micron particle size and drying and reducing with hydrogen at high space velocity at 100–500° C. temperature for 2–12 hours, then transferring the dried skeletal iron catalyst into water-free ethanol or liquid paraffin for storage.

* * * * *